United States Patent
Plenz et al.

(10) Patent No.: US 10,820,817 B2
(45) Date of Patent: Nov. 3, 2020

(54) MONITORING THE EFFECTS OF SLEEP DEPRIVATION USING NEURONAL AVALANCHES

(71) Applicant: The United States of America, as represented by the Secretary, Department of Health & Human Services, Rockville, MD (US)

(72) Inventors: Dietmar Plenz, Chevy Chase, MD (US); Oren Shriki, Rockville, MD (US); Giulio Tononi, Verona, WI (US); Christian Meisel, Washington, DC (US)

(73) Assignee: The United States of America, as represented by The Secretary of Defense, Armed Forces Institute of Pathology, Bethesda, MD (US)

( * ) Notice: Subject to any disclaimer, the term of this patent is extended or adjusted under 35 U.S.C. 154(b) by 290 days.

(21) Appl. No.: 14/912,392

(22) PCT Filed: Aug. 15, 2014

(86) PCT No.: PCT/US2014/051234
§ 371 (c)(1),
(2) Date: Feb. 16, 2016

(87) PCT Pub. No.: WO2015/023929
PCT Pub. Date: Feb. 19, 2015

(65) Prior Publication Data
US 2016/0198968 A1  Jul. 14, 2016

Related U.S. Application Data

(60) Provisional application No. 61/866,962, filed on Aug. 16, 2013.

(51) Int. Cl.
*A61B 5/0476* (2006.01)
*A61B 5/00* (2006.01)
(Continued)

(52) U.S. Cl.
CPC ........ *A61B 5/04001* (2013.01); *A61B 5/0478* (2013.01); *A61B 5/4806* (2013.01); *A61B 5/04017* (2013.01)

(58) Field of Classification Search
None
See application file for complete search history.

(56) References Cited

U.S. PATENT DOCUMENTS

| | | | | |
|---|---|---|---|---|
| 2002/0133088 A1* | 9/2002 | Heyrend | ............ | A61B 5/04842 600/544 |
| 2002/0183644 A1* | 12/2002 | Levendowski | ........ | A61B 5/048 600/544 |
| 2009/0036791 A1* | 2/2009 | Plenz | ................... | A61B 5/0476 600/544 |

OTHER PUBLICATIONS

Priesemann et al. Neuronal Avalanches Differ from Wakefulness to Deep Sleep—Evidence from Intracranial Depth Recordings in Humans. PLoS Computational Biology 9(3), 2013.*

(Continued)

*Primary Examiner* — Etsub D Berhanu
(74) *Attorney, Agent, or Firm* — Locke Lord LLP; Christopher J. Capelli; Judy R. Naamat

(57) ABSTRACT

The present invention is directed to a method of continuously monitoring neuronal avalanches in a subject comprising (a) determining a deviation in avalanche exponent ($\alpha$) or branching parameter ($\sigma$) from a predetermined value at rest, wherein the pre-determined value of $\alpha$ is a slope of a size distribution of the synchronized neuronal activity and the predetermined value is $-3/2$ and the pre-determined value of $\sigma$ is a ratio of successively propagated synchronized neuronal activity and the predetermined value is 1; and (b)

(Continued)

A.

B.

repeating step (a) one or more times to continuously monitor neuronal avalanches in a subject. The invention also features methods of determining or monitoring the degree of sleep deprivation in a subject, methods of identifying subjects that are susceptible to a sleep disorder and methods of diagnosing a sleep disorder in a subject.

12 Claims, 6 Drawing Sheets

(51) Int. Cl.
  *A61B 5/04* (2006.01)
  *A61B 5/0478* (2006.01)

(56) References Cited

OTHER PUBLICATIONS

Meisel et al. Fading Signatures of Critical Brain Dynamics during Sustained Wakefulness in Humans. The Journal of Neuroscience, Oct. 20, 2013, 33(44):17363-17372.*
Plenz, D., "Neuronal Avalanches and Coherence Potentials", The European Physical Hournal Special Topics, Springer-Verlag, Berlin/Heidelberg, vol. 205 No. 1, May 1, 2012, pp. 259 0 301; XPO35049153; ISSN: 1951-6401.
Viola Priesemann, et all, "Neuronal Avalanches Differ from Wakefulness to Deep Sleep—Evidence from Intracranial Depth Recordings in Humans", PLOS Computational Biology, vol. 9, No. 3, Mar. 21, 2013, XPO55143062; ISSN: 1553-734.
International Search Report and Written Opinion, for PCT/US2014/051234, dated Aug. 15, 2014.

\* cited by examiner

A.

B.

US 10,820,817 B2

MONITORING THE EFFECTS OF SLEEP DEPRIVATION USING NEURONAL AVALANCHES

RELATED APPLICATIONS

This application is the U.S. National Stage of PCT International Application No. PCT/GB2018/053323, filed Nov. 16, 2018, which claims the benefit of priority under 35 U.S.C. § 119(e) to U.S. Provisional Application No. 61/866, 962, filed Aug. 16, 2013, which applications are incorporated herein by reference in their entirety.

STATEMENT OF RIGHTS TO INVENTIONS MADE UNDER FEDERALLY SPONSORED RESEARCH

This work was supported by the National Institute of Neurological Disorders and Stroke (NINDS) under grant number R01NS055185 and by the National Institute of Mental Health (NIMH) under grant number 1P20MH-077967-01A1. The Government has certain rights in this invention.

FIELD OF THE INVENTION

This invention relates generally to the field of sleep and sleep deprivation.

BACKGROUND OF THE INVENTION

The beneficial role of sleep for brain function and cognitive processing is well documented [1-3]. For example, subjects who were trained on a motor-learning task in the evening and were tested in the morning 12 hours later, showed greater improvement in performance compared with subjects who were trained on the same task in the morning and were tested 12 hours later in the evening [3]. Conversely, it is also well demonstrated that deprivation from sleep has detrimental effects on cognitive function [4-6].

The breadth of mechanisms through which sleep exerts its beneficial functions is not well understood. At the level of the brain, though, the synaptic homeostasis hypothesis [7], has gained recognition in recent years. The hypothesis suggests that sleep regulates the strength of synaptic connections in the brain. In particular, synapses strengthened during wakefulness, e.g. during memory formation, eventually lead to an over-excitability of brain networks unless the balance between excitation and inhibition is appropriately re-established during sleep. Accordingly, sleep deprivation is predicted to lead to an imbalance between excitation and inhibition towards an excitation-dominated state, in line with an increased risk for epileptic seizures and hallucinations during prolonged periods of wakefulness.

Sleep deprivation increases the EEG power in the slow wave (0.5-4.5 Hz) and theta (5-9 Hz) range [8-10]. Although such increases in select frequency bands have been hypothesized to reflect changes in synaptic strength in the underlying neuronal circuits [7, 9], the relationship between EEG power and synaptic plasticity remains unclear. EEG power also depends on recording technique and differs among individuals, making it hard to devise absolute criteria for quantifying the effect of sleep deprivation.

An alternative metric for brain activity that has been shown to be sensitive to the balance of excitation and inhibition is based on the concept of neuronal avalanches [11]. Neuronal avalanches are intermittent, spatiotemporal activity bursts that emerge spontaneously in vitro [2, 12], in vivo [6, 10], and, more recently, in human resting brain activity [13]. Importantly, the sizes of neuronal avalanches distribute according to a power law with an exponent $\alpha=-3/2$. This signature of avalanches is in line with the finding that avalanches reflect exquisitely balanced propagation of neural activity captured by a critical branching parameter of $\sigma=1$ [11, 12, 14]. Manipulating the balance of excitation and inhibition leads to deviations from the power law behavior [15]. For example, blocking inhibition in cortical networks leads to epileptic-like behavior and to more large-size avalanches than what would be expected from a power law distribution [15]. Moreover, these deviations are accompanied by a decrease in performance in terms of various measures of information representation, transmission and storage [15, 16].

Sleep deprivation is known to adversely affect basic cognitive abilities such as object recognition and decision making, even leading to hallucinations and epileptic seizures. At the neuronal level, sleep deprivation is associated with an increase in synaptic excitation, suggesting that sleep restores the normal balance of excitation and inhibition in the brain. Currently, there is no easy way to identify the detrimental effects of sleep deprivation from monitoring brain activity directly. Accordingly, there is a need in the art for new methods for monitoring the effects of sleep deprivation.

SUMMARY OF THE INVENTION

The present invention provides a robust method to continuously monitor brain activity in order to estimate the potential decrease in behavioral and cognitive performance that can result from sleep deprivation. It has been shown that ongoing brain activity in humans organizes as neuronal avalanche dynamics. Avalanche dynamics are characterized by a power law in avalanche size distribution with an exponent of alpha $(\alpha)=-3/2$ and a critical branching parameter of sigma $(\sigma)=1$. It has been shown that neuronal networks that maintain neuronal avalanche dynamics, i.e. (alpha, sigma)=(-3/2, 1) optimize numerous aspects of information processing [14-16]. The present application demonstrates that a deviation from the optimal set of avalanche parameters correlates with duration of wakefulness and decrease in behavioral performances as measured in a simple reaction time task.

Accordingly, the invention monitors continuously brain activity by non-invasive means, e.g. EEG electrodes embedded into a helmet, and estimates neuronal avalanche parameters continuously. The deviation of current parameters from the optimal set (-3/2, 1) of avalanche parameters is continuously calculated. Decrease in performance positively correlates with deviation from the optimal set. A tolerance range will be introduced for tolerable degrees of deviation (e.g. 10%). Feedback signals to the human about deviation of the current brain state from avalanche dynamics will be provided. In certain embodiments, continuously recorded EEG will be evaluated on line, and if the deviation from expected avalanche dynamics reaches a critical threshold, an alert will be issued signaling, for example, that the subject is at risk of underperformance, or in post-exercise analysis to identify individuals resilient to sleep deprivation or risk.

In a first aspect, the method features methods of continuously monitoring neuronal avalanches in a subject comprising (a) determining a deviation in avalanche exponent $(\alpha)$ or branching parameter $(\sigma)$ from a predetermined value at rest, wherein the pre-determined value of $\alpha$ is a slope of a size distribution of the synchronized neuronal activity and the predetermined value is −3/2 and the pre-determined value of σ is a ratio of successively propagated synchronized neuronal activity and the predetermined value is 1; and (b) repeating step (a) one or more times to continuously monitor neuronal avalanches in a subject.

In one embodiment, the method further comprises (c) identifying the time when α and σ deviate from their predetermined values at rest. In another embodiment, step (a) comprises (i) continuously recording the electroencephalogram (EEG); (ii) filtering the EEG; (iii) detecting positive/negative threshold crossings at each EEG electrode; (iv) clustering threshold crossings on the EEG array on a predetermined time scale; (v) calculating the cluster size distribution and determining the slope alpha (α); and (vi) calculating the ratio of successive threshold crossing to obtain sigma (σ).

In another embodiment, the EEG is continuously recorded at more than one site, for example 2, 3, 4, 5, 6, 7, 8, 9, 10, 11, 12, 13, 14, 15, 16, 17, 18, 19, 20, 21, 22, 23, 24, 25 or more sites. In a related embodiment, the EEG is continuously recorded at more than 10 sites.

In a further embodiment, the EEG is filtered between 1-100 Hz.

In another further embodiment, the time scale is 1-50 ms, for example 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 ms.

In another aspect, the invention features a method of determining the degree of sleep deprivation in a subject comprising (a) determining a deviation in avalanche exponent (α) or branching parameter (σ) from a predetermined value at rest, wherein the pre-determined value of α is a slope of a size distribution of the synchronized neuronal activity and the predetermined value is −3/2 and the pre-determined value of σ is a ratio of successively propagated synchronized neuronal activity and the predetermined value is 1; and (b) repeating step (a) one or more times, wherein a change in α or σ from the pre-determined value indicates the degree of sleep deprivation in a subject.

In yet another aspect, the invention features a method of identifying subjects that are susceptible to a sleep disorder comprising (a) determining a deviation in avalanche exponent (α) or branching parameter (σ) from a predetermined value at rest, wherein the pre-determined value of α is a slope of a size distribution of the synchronized neuronal activity and the predetermined value is −3/2 and the pre-determined value of σ is a ratio of successively propagated synchronized neuronal activity and the predetermined value is 1; and (b) repeating step (a) one or more times, wherein a change in α or σ from the pre-determined value indicates that the subject is susceptible to a sleep disorder.

In still another aspect, the invention features a method of diagnosing a sleep disorder in a subject comprising (a) determining a deviation in avalanche exponent (α) or branching parameter (σ) from a predetermined value at rest, wherein the pre-determined value of α is a slope of a size distribution of the synchronized neuronal activity and the predetermined value is −3/2 and the pre-determined value of σ is a ratio of successively propagated synchronized neuronal activity and the predetermined value is 1; and (b) repeating step (a) one or more times, wherein a change in α or σ from the pre-determined value indicates that the subject is suffering from a sleep disorder.

In one embodiment of the above aspects, the determined value α is a slope of a size distribution that is steeper or more shallow than the pre-determined slope. In another embodiment of the above aspects, the determined value σ is a branching ratio that is smaller or larger than 1. In a further embodiment of the above aspects, the change in in α or σ from the pre-determined value is correlated with an increased reaction time in a psychomotor vigilance task. In another further embodiment of the above aspects, the change in α or σ from the pre-determined value is correlated with a decrease in behavioral performance.

In one embodiment, the subject is suffering from a sleep disorder.

In one embodiment, the subject has not slept for 24 or more hours, for example 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72 or more hours.

In one embodiment of the above aspects, the method further comprises determining the magnitude and spatial distribution of theta power.

In another embodiment of the above aspects, the method further comprises gathering data from other physiological sensors.

In a further embodiment of the above aspects, the method is operational with hardware or software or a combination thereof.

Definitions

To facilitate an understanding of the present invention, a number of terms and phrases are defined below.

As used herein, the singular forms "a", "an", and "the" include plural forms unless the context clearly dictates otherwise. Thus, for example, reference to "a biomarker" includes reference to more than one biomarker.

Unless specifically stated or obvious from context, as used herein, the term "or" is understood to be inclusive.

As used herein, the terms "comprises," "comprising," "containing," "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The term "behavioral performance" is meant to refer to performance in a cognitive task, such as, but not limited to, reaction time in a typical psychomotor vigilance task (PVT), a sensorimotor coordination task, such as steering a vehicle through demanding environment, or cognitive functions, such as decision making.

The term "continuously monitoring" is meant to refer to determining a value or output more than one time, for example two, three, four, five, six, seven, eight, nine, ten or more times with relatively short intervals between consecutive measurements.

The term "electroencephalogram (EEG)" is meant to refer to the recording of electrical activity, typically along the scalp.

The term "event" is meant to refer to a significantly large signal deflection in one of the recorded channels.

The term "neuronal avalanche" is meant to refer to a cascade of bursts of activity in neuronal networks. Neuronal avalanches reflect normal brain activity in the awake state.

The term "avalanche exponent" is meant to refer to the slope (α) of the power law in neuronal avalanche dynamics.

Preferably, the sizes of neuronal avalanches distribute according to a power law with an exponent $\alpha=-3/2$. A deviation in avalanche exponent ($\alpha$) from a predetermined value at rest is any change in $\alpha$.

The term "branching parameter" is meant to refer to a value ($\sigma$) that reflects the intrinsic amplification in cascades of activity. A deviation in branching parameter ($\sigma$) from a predetermined value at rest is any change in $\sigma$.

The term "sleep disorder" is meant to refer to generally any abnormal sleeping pattern. Examples of sleep disorders include, but are not limited to, dyssomnia, insomnia, sleep apnea, narcolepsy, and circadian rhythmic disorders.

The term "subject" is meant to refer to any form of animal. Preferably the subject(s) are mammal, and most preferably human.

The term "synchronized neuronal activity" is meant to refer to activity of a group of neurons. Synchronized neuronal activity can give rise to macroscopic oscillations or transient deflections, which can be observed in an electroencephalogram (EEG).

The term "theta power" is meant to refer to the power spectrum of the EEG signal in the theta frequency range, which is typically from 4-5 Hz to 8-9 Hz.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 1A is a line graph showing the cascade size distribution of a single subject using $\Delta t=6$ ms. Solid black line depicts original data and broken red line corresponds to a control, i.e. phase-shuffled data in which temporal correlations among EEG sensors are destroyed and avalanches are absent. Broken black line represents a reference power law with an exponent of $-3/2$. FIG. 1B is a line graph demonstrating the cascade size distributions for subsamples of the sensor array. Line color indicates the number of sensors used for the analysis.

FIG. 3A, FIG. 3C, and FIG. 3D are line graphs that show dependence of branching parameter (FIG. 3A), avalanche exponent (FIG. 3B) and reaction time (FIG. 3C) with time awake (mean across datasets). The red dot represents measurement after 8 hours of recovery sleep. Importantly, even a transient improvement in reaction time is accompanied with a corresponding transient return of the avalanche metrics towards the optimal values (alpha, sigma)=$(-3/2, 1)$ ($4^{th}$ time point=12 hrs wakefulness). FIG. 3D is a line graph that shows correlation between branching parameter and avalanche exponent during time awake. FIG. 3E is a line graph showing the correlation between branching parameter and RT during time awake. FIG. 3F is a line graph showing the dependence of mean inter event interval (IEI) on time awake. The p-values of the linear regression are displayed in each panel.

FIG. 4A is a line graph showing the change in power law of avalanche sizes with increase sleep deprivation in rats. Note tendency to supercritical dynamics (arrow; single experiment; shifted for visibility). Broken line: $-3/2$. FIG. 4B is a line graph showing avalanche metrics $\kappa$, i.e. the deviation from a power law with slope of $-3/2$, and $\sigma$ (z-scores) quantify the progressive deviation from avalanche dynamics for baseline (B), sleep deprivation in h, and after sleep (R) for n=3 rats.

FIG. 5A is a line graph showing the probability distribution of cascade sizes deviates from a power-law distribution in the tail (arrow) after sustained wakefulness. Curves represent combined avalanches from a subject for the first four EEG recordings (blue, 0-9 h of wakefulness) and the last four recordings (red, 30-39 h of wakefulness). FIG. 5B is a series of bar charts showing both $\sigma_n$ (branching parameter, left plot) and $\Delta D_n$ (indexing the deviation from a power-law function), right plot) progressively increased during sustained wakefulness (hours 0-39) and return to lower values after recovery sleep (ps). Values were normalized to z-scores in each subject before averaging over the different subjects, which is denoted by subscripts n. Gray curves show the continuous measurements, the colored bars correspond to averages of the four EEG recordings at 0-9 h (blue) and at 30-39 h (red) of wakefulness. The plot in the middle shows absolute means values of $\sigma$ over all individuals without prior normalization of the data at the beginning of sleep deprivation (blue) and toward the end (red). Error bars indicate SE. Parameters were $\Delta t=39$ ms, threshold=4.0, r=0.75; p values indicate the difference between red and blue bars (two-tailed paired t test). FIG. 5C is a bar chart showing the increase in $\sigma_n$ (gray bars) and $\Delta D_n$ (brown bars) is illustrated as the difference (Diff) between values at the end (30-39 h of wakefulness) and the beginning (0-9 h) of the sleep deprivation period. Positive values therefore indicate an increase of $\sigma_n$ or $\Delta D_n$ in the course of sleep deprivation, which was significant for a broad range of thresholds (th) and correlations (R, *p≤0.05, **p≤0.01; two-tailed paired t test). FIG. 5D is a bar chart showing recovery after sleep. Bars illustrate the decrease in $\sigma_n$ (gray bars) and $\Delta D_n$ (brown bars) after recovery sleep (ps) compared with the last value of the sleep deprivation period (after 39 h of wakefulness). Negative values therefore indicate a decrease of $\sigma_n$ or $\Delta D_n$ after recovery sleep following the 40 h sleep deprivation period. Differences were significant over a range of parameters.

DETAILED DESCRIPTION

Figure 1:
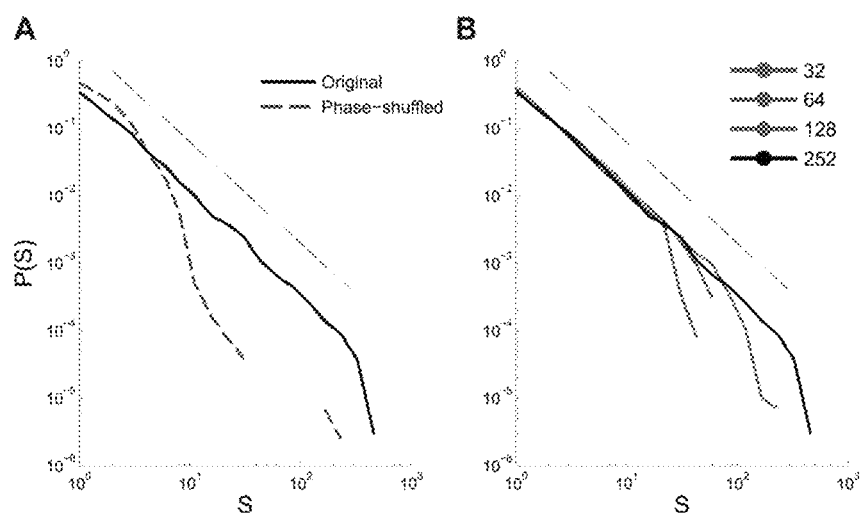
FIG. 1A and FIG. 1B show cascade size distributions follow power laws, as expected for neuronal avalanches.

Previous studies indicate that sleep deprivation increases the EEG power in the slow wave (0.5-4.5 Hz) and theta 4-5 Hz to 8-9 Hz range. Current approaches rely on analysis of these frequency bands. However, EEG power depends on recording technique and differs among individuals, making it hard to devise absolute criteria for quantifying the effect of sleep deprivation. Neuronal avalanches reflect normal brain activity in the awake state and are characterized by a power law in avalanche sizes with slope of −3/2 and a critical branching parameter of 1. In contrast to EEG power, the avalanche metric is an absolute metric that has been shown to be identical across individuals and it is directly related to the potential underlying imbalance of excitation and inhibition that results from sleep deprivation. This allows the metric to be used in absolute terms, i.e. no control group is required to identify performance changes. The present invention is based, at least in part, on the finding that after monitoring neuronal avalanches in the EEG of human subjects over the course of 36 hours of sleep deprivation, both the slope in size distribution and the branching parameter correlate with the duration of sleep deprivation as well as the increase in reaction time in a psychomotor vigilance task. The present invention demonstrates that avalanche dynamics provide absolute benchmarks to identify the decrease in performance for sleep deprived subjects.

Described herein is a clinical biomarker to monitor the quality and cumulative effect of sleep. Sleeping disorders constitute a broad spectrum of neurological and other medical conditions, whereby impaired quality of sleep often leads to severe health and cognitive defects. As such, effective clinical treatment and diagnosis would benefit from objective biomarkers quantifying the recuperational effect of sleep or its deficits. However, prior to the invention described herein, there was a lack of objective biomarkers measuring the quality of sleep. The results described herein demonstrate a marker relating cortical dynamics to optimal cognitive performance. As described herein, avalanche dynamics are re-established by sleep after prolonged wakefulness and highly correlate with behavioral performance.

Avalanche dynamics have also been shown to optimize a number of aspects in information processing in cortical networks suggesting a beneficial effect of sleep induced reset of avalanche dynamics for cognitive performance. In this regard, the metrics provide an objective marker for the quality of sleep and have the potential to guide and monitor the effect of treatment to improve sleep quality in clinical settings. Software extracting the markers related to neuronal avalanches is a useful tool for diagnostic and monitoring treatment progress in sleep laboratories and other clinical settings.

Also described herein is a biomarker for optimal cortical function under conditions of sustained wakefulness. In many professions long, uninterrupted shifts are required while maintaining high cognitive functioning, e.g., medical professions on call, military personnel, and pilots. The quantification of cortical dynamics by neuronal avalanches metrics has the opportunity to provide valuable and objective markers for cognitive performance under sleep deprivation conditions.

Neuronal Avalanches

Neuronal avalanches are intermittent, spatiotemporal activity bursts that emerge spontaneously in vitro, in vivo and in human resting brain activity. A definition of neuronal avalanches is provided in US Patent Application 20090036791, filed Feb. 5, 2009 and incorporated by reference in its entirety herein. A neuronal avalanche is a sequence of consecutive time bins of duration $\Delta t$ with at least one event, which is preceded and terminated by at least one time bin with no activity. The absence of activity for a period of $\Delta t$ thus indicates the end of an avalanche. If the decision of whether an avalanche has ended is made too early ($\Delta t$ too short), avalanches will be terminated prematurely; if the $\Delta t$ chosen is too long, avalanches will be falsely concatenated. If avalanches did simply propagate like a wave, an approximation for $\Delta t$ ($\Delta tavg$) could be obtained by averaging the time between one event at one sensor and the next event at neighboring sensors only. Because events in avalanches occur in irregular patterns across sensors on the array, a pair wise approximation can be used in order to assess the average time that is required for events to propagate between electrodes. It is noted that neuronal avalanches are scale-invariant. The identification of a particular $\Delta t$ for the analysis is only required because of the choice of a particular spatial sampling grid imposed by the sensor or electrode array used to measure events. It was shown [e.g. 11] that the choice of $\Delta t$ linearly scales with the choice of interelectrode or intersensor distance $\Delta t$ and thus the ratio $\Delta d / \Delta t =$ constant and approximates the average propagation velocity of neuronal synchronized bursts.

US Patent Application 20090036791 sets forth how to calculate $\Delta t$ avg for fixed intersensor/interelectrode distances of the array, and how to calculate avalanche size and avalanche branching parameter. In order to calculate $\Delta t$ avg, the distribution of time intervals T for successive events on the array can be obtained. Starting with the first event, e.g. $A^k(t_i)$ on electrode k at time $t_i$, the next occurrence of an event on the array can be searched for, e.g. $A^l(t_j)$ on electrode l at time $t_j$, and calculated the time interval $T_{m \cdot \Delta t}^{k,l}$, where $m = (t_j - t_i)/\Delta t$. This process can be repeated for all occurrences of events on electrode k and for all electrodes. The resulting values can be combined into one density distribution $P(T_{m \Delta t})$, which captures how often successive events occurred with a particular delay m times $\Delta t$ on the array irrespective of their spatial location. Consequently, the average value of T provides an approximation for $\Delta tavg$, the average time to wait before making a decision whether an event propagated on the array. However, this interval distribution is highly skewed, particularly when one compares the last event with the first event in successive avalanches that are separated by long times. In order to exclude time intervals from successive events that are barely correlated, a cut-off time $\tau_{max}$ can be calculated for which the average crosscorrelation function (ccf) for pair wise electrode comparisons $R_{ccf}(\tau)$ had decayed to negligible values. The ccf between electrodes k, l ($R_{ccf}^{k,l}(\tau)$) can be calculated as $$R_{ccf}^{k,l}(\tau) = \frac{\frac{1}{m_{max}} \sum_{m=1}^{m_{max}} A_{LFP}^{\prime k}(m \cdot \Delta t + \tau) A_{LFP}^{\prime l}(m \cdot \Delta t)}{\sigma(A_{LFP}^{\prime k}) \sigma(A_{LFP}^{\prime l})} \quad (1)$$

at $\Delta t = 1$ ms for $\tau \ni [-100, 100]$, where m is an integer value up to $m_{max}$, $\Delta t + \tau < T_{tot}$, $A^{\prime k}(t_i) = A^k(t_i) - E(A^k)$, $E(.)$ is the expected value for $A^k(t_i)$, and $\sigma^2(.)$ is the variance. Finally, the population ccf ($R_{ccf}(\tau)$) can be calculated as $$R_{ccf}(\tau) = \frac{2}{n_{elec}(n_{elec}-1)} \sum_{k=1}^{n_{elec}} \sum_{l=k+1}^{n_{elec}} R_{ccf}^{k,l}(\tau) \qquad (2)$$

The estimate of the average time between successive, correlated nLFPs on the array, i.e. $\Delta t'_{avg}$, can be obtained by integrating the density distribution of intervals for each network Up to $\tau_{max}$, $$\Delta t'_{avg}(\tau_{max}) = \sum_{m=1}^{m \cdot \Delta t = \tau_{max}} T_{m \cdot \Delta t} P(T_{m \cdot \Delta t}) \qquad (3)$$

If the exemplary maximal sampling rate was 1 kHz, the actual $\Delta tavg$ to calculate avalanches can be taken as the nearest multiple of $\Delta t=1$ ms. In short, after $\Delta tavg$ is calculated for a particular network and experimental condition, the electrode signals can be re-sampled at the new temporal resolution of $\Delta tavg$. Time and amplitude of event peaks can be extracted as $A^k(t_i)$, where $t_i = i \cdot tavg$, $i\varepsilon \cdot [1, n'_{max}]$ and $T_{tot} = n'_{max} \cdot \Delta tavg$. Avalanches can be determined on the downsampled data set at bin width $\Delta tavg$.

Avalanche sizes can be calculated in two different ways. By taking into account event peak amplitudes $A_i^k$, the avalanche size $s_{FLP}^{Avalj}$ can be calculated by summing up $A_i^k$ on active electrodes for the lifetime $T^{AvaljLFP} = m$ times $\Delta tavg$ of $Aval_j$, defined as the number of m bins of width $\Delta tavg$ that were occupied by avalanche $Aval_j$ that started at time $t_i$ and stopped at time $t_i + (m-1) \cdot \Delta tavg$ $$s_{LFP}^{Avalj} = \sum_{i=0}^{m-1} \sum_{k=1}^{n_{elec}} A_{t_i + m \cdot \Delta t_{avg}}^k \qquad (4)$$

For the density distribution of $s_{LFP}$ or $S_{event}$, the range in sizes $s_{LFP}$ or $S_{event}$ was covered by 100 bins that increased logarithmically from 3-3000 µV (or any other event amplitude measure), which results in equidistant sampling of the data in logarithmic coordinates. Avalanche sizes can also be calculated as the number of active electrodes within an avalanche, see, using (4), but setting all non-zero $A_i^k$ values to 1. For the density distribution of $s_{ele}$, linear binning from 1 to the maximal number of array electrodes can be used. In the critical state, the distribution of avalanche sizes forms a power law with slope $\alpha = -3/2$. From the experimental data, the exponent $\alpha$ of the power law represents the slope of the log-log transformed size distribution and can be estimated using linear regression analysis. Estimating $\alpha$ is not limited to regression analysis only. For example, $\alpha$ can be estimated using a maximum likelihood estimation $$-\alpha = 1 + n \left[ \sum_{i=1}^{n} \ln \frac{N(s_i)}{N(s_{min})} \right]^{-1} \qquad (5)$$

where $N(s_i)$ represents the number of avalanches of size $s_i$, $N(s_{min})$ represents the number of minimal avalanche size $s_{min}$ measured, and n represents the number of size categories up to the cut-off imposed by the array size. Alternatively, $\alpha$ can be estimated from the cumulative size distribution up to the power law cut-off, which forms a slope of $\alpha + 1$. Because no significant differences exist between estimates of $\alpha$ based on SL ($\alpha_{LFP}$) or ($s_{ele}$) ($\alpha_{ele}$) slope values can be given as $\alpha_{LFP}$ unless a particular emphasis is placed on the area an avalanche covers on the array. Average avalanche size distributions can be plotted as mean+/−S.E.M.

The branching parameter $\sigma$ can be used to describe the balance of propagated synchronized activity in cortical tissue. The general definition of $\sigma$ refers to the ratio between successive generations, for example the average number of descendants from one ancestor. When $\alpha = -3/2$, the neuronal tissue is critical and, correspondingly, $\sigma = 1$. The branching parameter $\sigma$ can be defined in binary and analog terms.

In the binary case, $\sigma$ is defined as the average ratio of electrodes activated in time bin $\Delta t_{n+1}$ (descendants; $n_d$), divided by the number of electrodes active in time bin $\Delta t_n$ (ancestor; $n_a$). Mathematically, the average branching parameter $\sigma$ for the electrode array in the case of one ancestor electrode ($n_a=1$) is simply given by $$\sigma = \sum_{d=0}^{n_{max}} d \cdot p(d) \qquad (6)$$

where d is the number of electrode descendants, p(d) is the probability of observing d descendants, and $n_{max}$ is the maximal number of active electrodes. Note that formula (6) does not describe a probability density and theoretically $\sigma$ can take any valueless than or equal to zero. In the binary case, $\sigma$ is best estimated from the first and second time bin of an avalanche. Although strictly speaking, $\sigma$ is only defined for one ancestor, $\sigma$ can also be estimated when there are multiple ancestors. Under these conditions, d is given by $$d = \text{round}\left(\frac{n_d}{n_a}\right) \qquad (7)$$

where $n_a$ is the number of electrode ancestors observed in the first time bin and $n_d$ is the number of active electrodes in the second time bin of an avalanche and round is the rounding operation to the nearest integer. The likelihood of observing d descendants can be approximated by:

$$p(d) = \sum_{avalanches} \left(\frac{n_{\Sigma a|d}}{n_{\Sigma a}}\right) \cdot \left(\frac{n_{max} - 1}{n_{max} - n_a}\right) \qquad (8)$$

where $n_{\Sigma n|d}$ is the total number of electrode ancestors in all avalanches when $n_d$ descendants were observed, $n_{\Sigma a}$ is the total number of ancestors observed in all avalanches, and $$\left(\frac{n_{max} - 1}{n_{max} - n_a}\right) \qquad (9)$$

is a factor that provided an approximate correction for the reduced number of electrodes available in the next time bin because of electrode refractoriness. Note that the branching parameter is not defined for zero ancestors and thus does not provide information about the initiation of bursts. In cases where there is only one ancestor, formula (8) is equivalent to (6). In the analog case, the branching parameter $\sigma$ includes analog information about the event, e.g. its negative peak value (event amplitude) or the event area (e.g. integrated event amplitude from crossing negative threshold to return to threshold).

For the analog calculation, each event in an avalanche is normalized to the amplitude or area of the first event in the avalanche. For each time bin, the corresponding event distributions from all avalanches can be combined. The succession of event distributions during the life time of the avalanche then approximates the branching parameter σ. More specifically, if the mode (mod) of the event distributions equals 1 for each time bin, events do not grow nor do they decay within an avalanche, which is equivalent to the binary case of σ=1. Because the distribution of ratios is better expressed in log values, in the analog case, one can state log(1)=0. Thus, log(mod)=0 demonstrates that the brain dynamics is critical and fulfills the criteria for neuronal avalanches.

US Patent Application 20090036791 also provides methods and systems for performing a Neuronal Avalanche Assay (NAS-assay). The NAS-assay uses the spatial distribution of synchronized activity, in neuronal tissue. For exemplary purposes, the description is directed toward the NAS-assay using local field potentials (LFP). In the LFP, the activity of a single neuron is barely detectable, however, if many neurons synchronize their activities, the LFP is large enough to be registered by a local recording device, in this case, the microelectrode. As LFPs propagate along an array of microelectrodes, the neuronal activity can be analyzed for neuronal avalanches. However, any method with which synchronized neuronal activity can be detected locally in the living brain and which allows for the monitoring of the spread of synchronized activity, can be used in the NAS-assay. The NAS-assay, in its principle design, is not limited to the use of LFPs only.

Methods

In certain aspects, the present invention features methods of continuously monitoring neuronal avalanches in a subject. In preferred embodiments, the method comprises (a) determining a deviation in avalanche exponent (α) or branching parameter (σ) from a predetermined value at rest, wherein the pre-determined value of α is a slope of a size distribution of the synchronized neuronal activity and the predetermined value is −3/2 and the pre-determined value of σ is a ratio of successively propagated synchronized neuronal activity and the predetermined value is 1; and (b) repeating step (a) one or more times (e.g. 1, 2, 3, 4, 5, 6, 7, 8, 9, 10, 11, 12, 13, 14, 15, 16, 17, 18, 19, 20, 25, 30, 35, 40, 45, 50 or more times) to continuously monitor neuronal avalanches in a subject. The method may further comprise (c) identifying the time when α and σ deviate from their predetermined values at rest.

In certain exemplary embodiments, step (a) comprises (i) continuously recording the EEG; (ii) filtering the EEG; (iii) detecting positive/negative threshold crossings at each EEG electrode; (iv) clustering threshold crossings on the EEG array on a predetermined time scale; (v) calculating the cluster size distribution and determining the slope alpha (α); and (vi) calculating the ratio of successive threshold crossing to obtain sigma (σ).

EEG signals can be obtained by any method known in the art, or subsequently developed by those skilled in the art to detect these types of signals. Sensors include but are not limited to electrodes or magnetic sensors. Preferably, the EEG is continuously recorded at >10 sites.

The EEG recording is characterized by amplitude, frequency and their change over time. The frequency component of the EEG can be utilized to infer the level of an individual's neural activity. The frequencies are broken down into ranges which describe how alert and conscious a person is at any given time. The delta frequency (1-4 Hz) is associated with deep sleep. The theta frequency (4-5 Hz to 8-9 Hz) is associated with drowsiness, and delta activity is also common. The alpha frequency (8-13 Hz) is associated with relaxed wakefulness, where not much brain resources are devoted to any one thing. The beta frequency (12-20 Hz, or 30 Hz) and the gamma frequency (36-44 Hz) are associated with alert attentiveness In certain embodiments, the EEG is filtered between 1-100 Hz.

If electrodes are used to pick up the brain wave signals, these electrodes may be placed at one or several locations on the subject(s)' scalp or body. The electrode(s) can be placed at various locations on the subject(s) scalp in order to detect EEG or brain wave signals. Common locations for the electrodes include frontal (F), parietal (P), anterior (A), central (C) and occipital (O). Preferably for the present invention at least one electrode is placed in the occipital position. In order to obtain a good EEG or brain wave signal it is desirable to have low impedances for the electrodes. Typical EEG electrodes connections may have an impedance in the range of 5 to 10 K ohms. It is in general desirable to reduce such impedance levels to below 2 K ohms. Therefore a conductive paste or gel may be applied to the electrode to create a connection with an impedance below 2 K ohms. Alternatively, the subject(s) skin may be mechanically abraded, the electrode may be amplified or a dry electrode may be used. Dry physiological recording electrodes of the type described in U.S. patent application Ser. No. 09/949,055 are herein incorporated by reference. Dry electrodes provide the advantage that there is no gel to dry out, no skin to abrade or clean, and that the electrode can be applied in hairy areas such as the scalp. Additionally if electrodes are used as the sensor(s), preferably at least two electrodes are used—one signal electrode and one reference electrode; and if further EEG or brain wave signal channels are desired the number of electrodes required will depend on whether separate reference electrodes or a single reference electrode is used. For the various embodiments of the present invention, preferably an electrode is used and the placement of at least one of the electrodes is at or near the occipital lobe of the subject's scalp.

In certain embodiments, the time scale of performing the method is 1-50 ms, for example 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 ms.

In other aspects the invention provides methods of determining the degree of sleep deprivation in a subject or methods of identifying subjects that are susceptible to a sleep disorder, comprising (a) determining a deviation in avalanche exponent (α) or branching parameter (σ) from a predetermined value at rest, wherein the pre-determined value of α is a slope of a size distribution of the synchronized neuronal activity and the predetermined value is −3/2 and the pre-determined value of σ is a ratio of successively propagated synchronized neuronal activity and the predetermined value is 1; and (b) repeating step (a) one or more times (e.g. 1, 2, 3, 4, 5, 6, 7, 8, 9, 10, 11, 12, 13, 14, 15, 16, 17, 18, 19, 20, 25, 30, 35, 40, 45, 50 or more times), wherein a change in α or σ from the pre-determined value indicates the degree of sleep deprivation in a subject or wherein a change in α or σ from the pre-determined value indicates that the subject is susceptible to a sleep disorder.

The present invention also provides in other aspects methods of diagnosing a sleep disorder in a subject. The methods preferably comprise (a) determining a deviation in avalanche exponent (α) or branching parameter (σ) from a predetermined value at rest, wherein the pre-determined value of α is a slope of a size distribution of the synchronized neuronal activity and the predetermined value is −3/2 and the pre-determined value of σ is a ratio of successively propagated synchronized neuronal activity and the predetermined value is 1; and (b) repeating step (a) one or more times (e.g. 1, 2, 3, 4, 5, 6, 7, 8, 9, 10, 11, 12, 13, 14, 15, 16, 17, 18, 19, 20, 25, 30, 35, 40, 45, 50 or more times), wherein a change in α or σ from the pre-determined value indicates that the subject is suffering from a sleep disorder.

In certain embodiments, the determined value α is a slope of a size distribution that is steeper or more shallow than the pre-determined slope. For sleep deprivation, alpha gets smaller with wakefulness. The change in alpha can be a change in both directions (steeper/shallower).

In other embodiments, the determined value σ is a branching ratio that is smaller or larger than 1.

In exemplary embodiments, the change in α or σ from the pre-determined value is correlated with a decrease in behavioral performance, as reflected through an increased reaction time in a psychomotor vigilance task.

Preferably, the subject(s) are mammal, and more preferably human. The methods described herein can be used in subjects that experience prolonged periods of wakefulness (e.g. the subject has not slept for 24, 36, 48, 72 or more hours), for example, but not limited to, subjects on duty and in patients with sleep disorders. Typical applications may be related to many civil and military professions. Other subjects may be those post-exercise, wherein the methods described herein are used to identify individuals resilient to sleep deprivation or at risk.

The subjects of the present invention may be suffering from a sleep disorder. A sleep disorder is meant to refer to any abnormal sleeping pattern. Examples of sleep disorders include, but are not limited to, dyssomnia, insomnia, sleep apnea, narcolepsy, and circadian rhythmic disorders.

In certain embodiments, the invention may include a step for determining whether the subject maintained a normal sleeping pattern. This step can be performed or accomplished in a number of ways. In the simplest form, the subject can be questioned regarding his or her previous sleep patterns. In a somewhat more complex form the subject can be requested to fill out a questionnaire, which then can be graded to determine whether his or her previous sleep patterns where normal (or appeared normal). In an even more complex form the subject might undergo all night polysomnography to evaluate the subject's sleep architecture (e.g., obtaining respiratory disturbance index to diagnose sleep apnea). It is clear that there are numerous ways beyond those examples previously mentioned of determining whether the subject being analyzed had, or thought they had, a normal sleeping pattern, and therefore the examples given above are included as exemplary rather than as a limitation, and those ways of determining whether the subject maintained or thought they were maintaining a normal sleeping pattern known to those skilled in the art are considered to be included in the present invention.

In any of the methods described herein, the method may comprise a further step of gathering data from other physiological sensors of brain activity. For example magnetoencephalography (MEG), functional MRI (fMRI) using the BOLD signal or other related measures, optical imaging using fluorescent dyes that track neuronal activity such as intracellular calcium sensors, implanted microelectrode arrays to record the local field potential (LFP) or electrocorticogram (ECoG). In other embodiments, the method may comprise a step of gathering data related to typical signs of sleepiness, such as increased eye blink and/or yawning frequency.

On-Line Evaluation

The methods of the present invention can be operational with numerous other general purpose or special purpose computing system environments or configurations. Examples of well known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, smart phones, network PCs, minicomputers, mainframe computers, distributed computing environments that comprise any of the above systems or devices, and the like.

The methods of the present invention can be described in the general context of computer instructions, such as program modules, being executed by a computer. Generally, program modules comprise routines, programs, objects, components, data structures, etc. that perform particular tasks or implement particular abstract data types. The systems and methods of the present invention can also be practiced in distributed computing environments where tasks are performed by remote processing devices that are linked through a communications network. In a distributed computing environment, program modules can be located in both local and remote computer storage media including memory storage devices.

The methods of the present invention can be operational with hardware or software to allow continuous monitoring of subjects, for example subjects under extended wake periods. The proposed metrics will be implemented in software or hardware and will allow continuous monitoring of subjects under extended wake periods. In certain embodiments, continuously recorded EEG will be evaluated on line, and if the deviation from expected avalanche dynamics reaches a critical threshold, an alert will be issued signaling, for example, that the subject is at risk of underperformance, or in post-exercise analysis to identify individuals resilient to sleep deprivation or risk.

One skilled in the art will appreciate that the methods disclosed herein can be implemented via a general-purpose computing device in the form of a computer. The components of the computer can comprise, but are not limited to, one or more processors or processing units, a system memory, and a system bus that couples various system components including the processor to the system memory. Further, the methods of the present invention can be operational with numerous general purpose or special purpose computing system environments or configurations. Examples of well-known computing systems, environments, and/or configurations that can be suitable for use with the systems and methods comprise, but are not limited to, personal computers, server computers, laptop devices, smartphones, and multiprocessor systems. Additional examples comprise set top boxes, programmable consumer electronics, network PCs, minicomputers, mainframe computers, distributed computing environments that comprise any of the above systems or devices, and the like.

The methods of the present invention can be described in the general context of computer instructions, such as program modules, being executed by a computer. Generally, program modules comprise routines, programs, objects, components, data structures, etc. that perform particular tasks or implement particular abstract data types. The systems and methods of the present invention can also be practiced in distributed computing environments where tasks are performed by remote processing devices that are linked through a communications network. In a distributed computing environment, program modules can be located in both local and remote computer storage media including memory storage devices.

One skilled in the art will appreciate that the systems and methods disclosed herein can be implemented via a general-purpose computing device in the form of a computer. The components of the computer can comprise, but are not limited to, one or more processors or processing units, a system memory, and a system bus that couples various system components including the processor to the system memory.

The system bus represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (USA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI) bus also known as a Mezzanine bus. The bus, and all buses specified in this description can also be implemented over a wired or wireless network connection and each of the subsystems, including the processor, a mass storage device, an operating system, NAS software, neuronal data, a network adapter, system memory, an Input/Output Interface, a display adapter, a display device, and a human machine interface, can be contained within one or more remote computing devices at physically separate locations, connected through buses of this form, in effect implementing a fully distributed system.

The computer typically comprises a variety of computer readable media. Exemplary readable media can be any available media that is accessible by the computer and comprises, for example and not meant to be limiting, both volatile and non-volatile media, removable and non-removable media. The system memory comprises computer readable media in the form of volatile memory, such as random access memory (RAM), and/or non-volatile memory, such as read only memory (ROM). The system memory typically contains data such as neuronal data and/or program modules such as operating system and NAS software that are immediately accessible to and/or are presently operated on by the processing unit.

The computer can also comprise other removable/non-removable, volatile/non-volatile computer storage media. For example, and not meant to be limiting, a mass storage device can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device, including by way of example, an operating system and NAS software. Each of the operating system and NAS software (or some combination thereof) can comprise elements of the programming and the NAS software. Neuronal data can also be stored on the mass storage device. Neuronal data can be stored in any of one or more databases known in the art. Examples of such databases comprise, DB2, MICROSOFT Access, MICROSOFT SQL Server, ORACLE, mySQL, PostgreSQL, and the like. The databases can be centralized or distributed across multiple systems.

The user can enter commands and information into the computer via an input device (not shown). Examples of such input devices comprise, but are not limited to, a keyboard, pointing device (e.g., a "mouse"), a microphone, a joystick, a scanner, and the like. These and other input devices can be connected to the processing unit via a human machine interface that is coupled to the system bus, but can be, connected by other interface and bus structures, such as a parallel port, game port, an IEEE 1394. Port (also known as a Firewire port), a serial port, or a universal serial bus (USB).

A display device can also be connected to the system bus via an interface, such as a display adapter. It is contemplated that the computer can have more than one display adapter and the computer can have more than one display device. For example, a display device can be a monitor, an LCD (Liquid Crystal Display), or a projector. In addition to the display device, other output peripheral devices can comprise components such as speakers (not shown) and a printer (not shown) which can be connected to the computer via Input/Output Interface.

A neuronal activity detector can communicate with the computer via Input/Output Interface or across a local or remote network. In one aspect, users utilize a neuronal activity detector that is capable of collecting neuronal data. It will be appreciated that the neuronal activity detector can be any type of neuronal activity detector, for example and not meant to be limiting, a microelectrode array (to record LFPs and single/multi-unit activity), a surface electrode system (to record the EEG or ECoG), a charge-coupled device camera (CCD) or photodiode array (to record activity-dependent fluorescence changes), a magnetometer type SQUID (superconducting quantum interference device) sensor (to record the MEG), a functional magnetic resonance imaging (fMRI) device to measure the activity related blood oxygen-level dependent signal (BOLD), and the like. In another aspect, the neuronal activity detector can be an independent stand alone device, or can be integrated into another device. Optionally, the communication with computer via Input/Output Interface can be via a wired or wireless connection.

The computer can operate in, a networked environment using logical connections to one or more remote computing devices. By way of example, a remote computing device can be a personal computer, portable computer, a server, a router, a network computer, a peer device or other common network node, and so on. Logical connections between the computer and a remote computing device can be made via a local area network (LAN) and a general wide area network (WAN). Such network connections can be through a network adapter. A network adapter can be implemented in both wired and wireless environments. Such networking environments are conventional and commonplace in offices, enterprise-wide computer networks, intranets, and the Internet.

An implementation of NAS software can be stored on or transmitted across some form of computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any method or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods can employ Artificial Intelligence techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

The processing of the disclosed systems and methods of the present invention can be performed by software components. The disclosed systems and methods can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed methods can also be practiced in grid-based and distributed computing environments where tasks are performed by remote processing devices that are linked through a communications network. In a distributed computing environment, program modules can be located in both local and remote computer storage media including memory storage devices.

The NAS Software allows for the study of neuronal avalanches and includes many analysis features. NAS Software allows for the calculation of alpha ($\alpha$), the slope of the avalanche size distribution, and sigma ($\sigma$), the branching parameter at the correct temporal resolution ($\Delta t_{avg}$). Avalanche calculation controls set the parameters for concatenating neuronal events into avalanches. A multi-function control window contains functions that extract the avalanche parameters $\alpha$ and $\sigma$ at corresponding $\Delta t_{avg}$. For visual control, avalanche size distributions in log-log coordinates can be generated and displayed. Crosscorrelation plots used to calculate $\Delta t_{avg}$ can also be displayed at various temporal resolutions. Additional features relate to the identification and labeling of recording locations to superficial cortical layers in which avalanches occur. For example, the NAS Software allows for the topological identification of electrode positions on a microelectrode array with respect to brain region and cortical layer. NAS Software allows for the storage of spatial information, e.g. images, and miscellaneous data specific to an experimental configuration.

NAS Software can analyze the similarity in spatiotemporal organization between neuronal avalanches. The spatiotemporal organization of avalanche is highly diverse and the diversity can be used to further evaluate the quality of the data and to quantify the critical state in the cortical network. More specifically, the size distribution of significant avalanche families reveals a heavy-tail in family sizes that forms a power law with slope gamma. Shuffle and cluster controls allow for the generation of shuffled data sets and statistical evaluation of family significance and calculation of gamma. Several additional features allow for a detailed examination of avalanche similarity on which the family size distribution is based. An avalanche generation tree can be generated that represents the generational relationship between avalanches based on similarity. An avalanche similarity matrix can be generated that contains the similarity index for all possible pair wise comparisons between avalanches. A multi-function control window for cluster analysis contains functions for studying the spatiotemporal organization of avalanches, for example, displaying a family frequency distribution plot to derive gamma.

NAS Software allows for visualization and editing of the temporal organization of neuronal avalanches. This can play a role when judging the quality of recorded data. An overview plot of LFP activity can be generated that displays the occurrence of LFPs during an experiment. A zoom view can display LFP occurrence for the temporal duration indicated by a colored rectangle in an overview plot. This allows for a detailed examination of avalanches and can be used to clean data sets from spurious noise. It also allows for the indication of avalanche extent and precise labeling of individual avalanches within a data set with respect to rank of occurrence in time, corresponding family and order within a family. For evoked activity, this feature can display identified stimuli and corresponding evoked avalanches. Family controls can display the type and occurrence of families over time. The family control and avalanche zoom view can be aligned in time for precise comparison.

Apparatus

According to various embodiments, an EEG headset is provided to subjects for use at home, recreational, at work, as well as in laboratory environments. In particular embodiments, the EEG headset includes multiple dry electrodes individually isolated and amplified. Data from individual electrodes may be processed prior to continuous transmission to a data analyzer. The continuously recorded EEG can be evaluated online as described herein and in US 20090036791, incorporated by reference in its entirety herein. For example, the methods described herein are used by consumers to monitor sleep deprivation in real time, e.g., on a smart phone.

Typical applications of the methods described herein are related to many civil and military professions, although not limited as such. A subject may wear the portable neuroresponse data collection mechanism during a variety of activities in non-laboratory settings. This allows collection of data from a variety of sources while a subject is in a natural state. For example, dry EEG electrodes can be easily integrated into helmets of pilots and soldiers to monitor the EEG. The present inventors have demonstrated that the avalanche metric is evident even when using a relatively small set of sensors. The continuously recorded EEG can be evaluated online, and if the deviation from expected avalanche dynamics reaches a critical threshold, an alert will be issued signaling that the subject wearing the helmet is at risk of underperformance.

In certain aspects, EEGs are recorded by a wireless EEG headset.

In certain aspects, the invention features an integrated program that includes the methods described herein performed with an EEG headset, for example a wireless headset. The methods can be performed in the comfort of the subject's home or workplace. The data are reviewed by a specialist after upload and can be used for diagnosis or intervention, and can be made through an integrated webportal. The portal allows for on-going clinician monitoring of progress.

EXAMPLES

It should be appreciated that the invention should not be construed to be limited to the examples that are now described; rather, the invention should be construed to include any and all applications provided herein and all equivalent variations within the skill of the ordinary artisan.

Example 1: Neuronal Avalanches and Sleep Deprivation

The present invention is based, in part, on the hypothesis that neuronal avalanche dynamics may be used to assess the effect of sleep deprivation in single subjects by following changes in metrics such as the avalanche exponent, $\alpha$, and the branching parameter, $\sigma$, over time. This hypothesis was tested with high density EEG (hd-EEG) recordings from human subjects during 36 hrs of sleep deprivation. It was found that indeed both avalanche metrics correlated with sleep deprivation and corresponding decrease in behavioral performance.

First, neuronal avalanches were looked for in the baseline recordings. FIG. 1A depicts the distribution of avalanche sizes from a single subject (solid black curve; $\Delta t=6$ ms), showing a clear power law behavior (broken black line represents a reference power law with an exponent of $-3/2$). A maximum likelihood based analysis (see Materials and Methods; [21, 22]) demonstrates a significantly better fit to a power law compared to an exponential function ($p<10^{-5}$ for all subjects). The power law reflects long-range spatiotemporal correlations among sensors. Accordingly, destroying the correlations among sensors by shuffling the phases of different frequency components in each sensor (while maintaining the power spectrum) destroys the power law behavior (FIG. 1A, broken red curve).

Finite-size scaling was demonstrated by dividing the original sensor array into sub-arrays of different sizes and recalculating the avalanche distribution for each size. The resulting distributions are shown in FIG. 1B (see color key for the number of sensors used in each case). A clear power law behavior was obtained in all cases with the cutoff proportional to the number of sensors used in line with the expectation for neuronal avalanches. The recording was made with eyes open and similar power law behavior was obtained with eyes closed.

Figure 2:
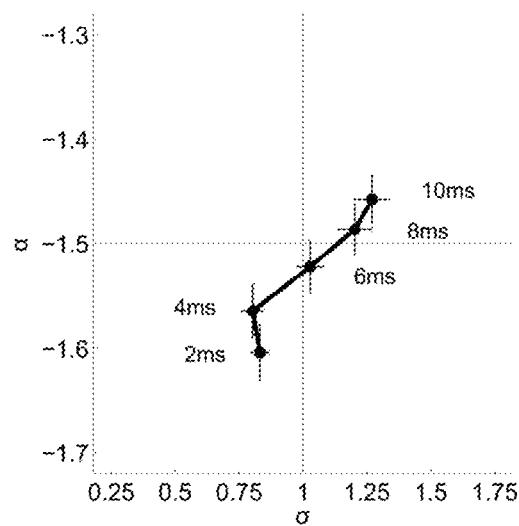
FIG. 2 shows the power law exponent is close to $\alpha=-3/2$ at the critical branching parameter $\sigma=1$. Phase plot of the power law exponent, $\alpha$, versus the branching parameter, $\sigma$. Each point represents the mean across datasets and error bars represent SEM.

The values of $\sigma$ and $\alpha$ monotonically increase with the time bin used to identify avalanches. FIG. 2 demonstrates this increase in $\alpha$ and $\sigma$ for time scales from 2 ms to 10 ms. Importantly, at the time scale of 6 ms, the branching parameter, $\sigma$, is close to 1 and the avalanche exponent, $\alpha$, is close to $-3/2$, in line with predictions from the theory of critical branching processes. The time scale of 6 ms is also the one used in FIG. 1.

Figure 3:
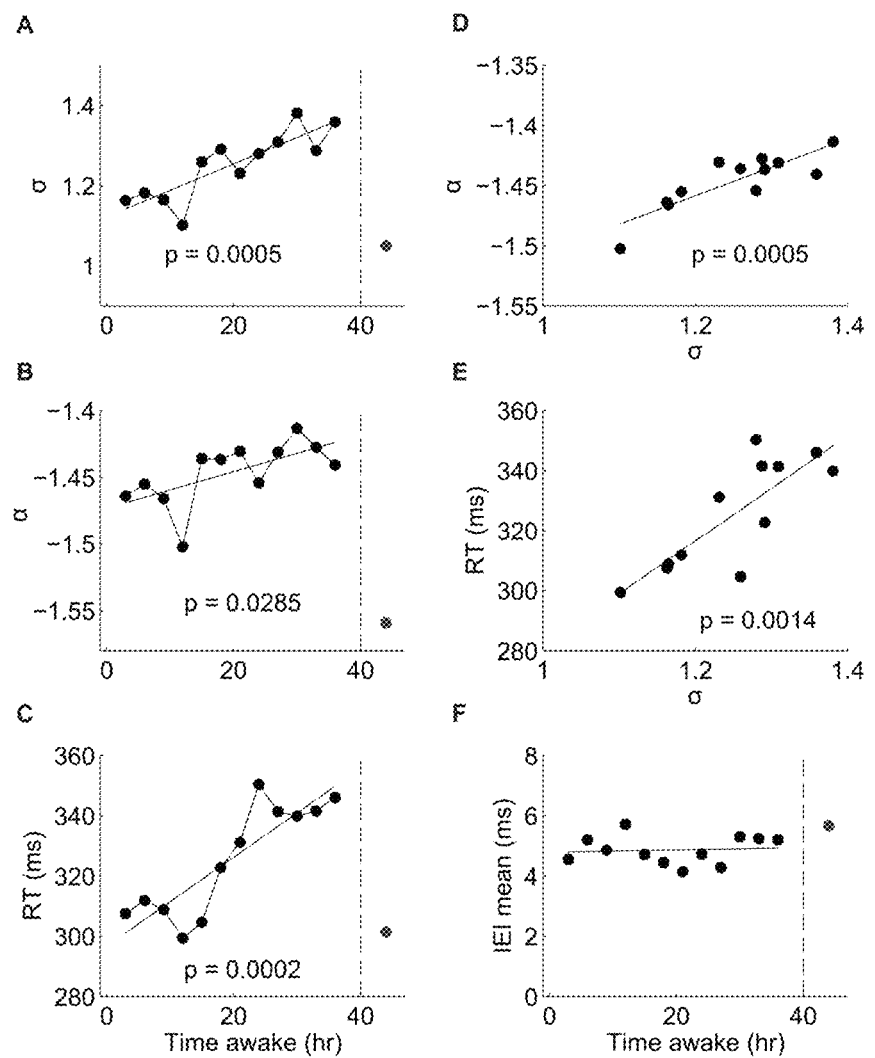
FIG. 3A-FIG. 3F show avalanche metrics correlate with sleep deprivation and decrease in behavioral performance.
Figure 4:
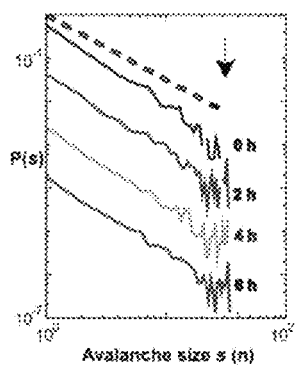
FIG. 4A and FIG. 4B are a series of line graphs showing an increase in deviation from avalanche dynamics with sleep deprivation in rats.
Figure 4:
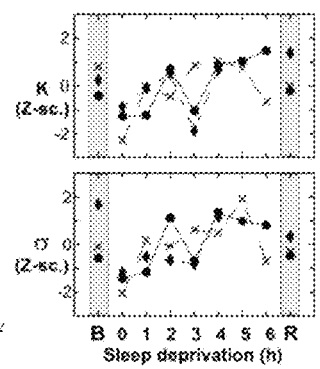
Figure 5:
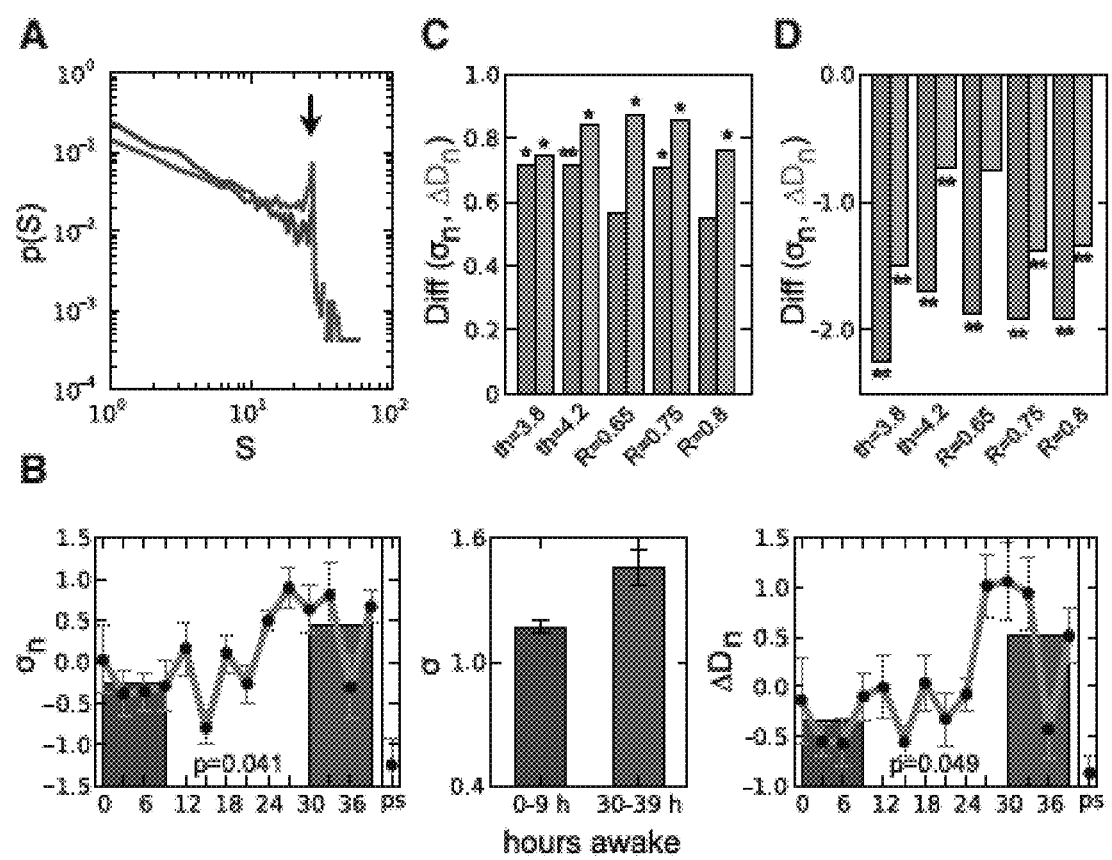
FIG. 5A-FIG. 5D are a series of bar charts and line graphs showing changes in the organization of neuronal avalanches with increasing duration of wakefulness.

Next, the avalanche analysis was applied to EEG recordings collected every 3 hrs during an extended wake period of 36 hours (see Material and Methods and [9]). FIGS. 3A and B depict the mean branching parameter and the mean avalanche exponent as a function of time awake (mean value at each time point was calculated from 5 different datasets). Both branching parameter and avalanche exponent increased with time awake (solid lines represent linear regression and the corresponding p-values are shown in each panel). They also had a similar envelope and were clearly correlated (FIG. 3D). The red dot in each plot marks the results after recovery sleep of at least 8 hours, indicating a strong recovery effect, which led to values even lower than the baseline.

In addition to EEG, subjects were evaluated using a 10-min psychomotor vigilance task (see Materials and Methods). The mean reaction time (RT) in this task followed a very similar pattern to that of $\alpha$ and $\sigma$ (FIG. 3C) and was highly correlated with $\sigma$ (FIG. 3E). Importantly, even a transient improvement in reaction time is accompanied with a corresponding, transient approach of the avalanche measures of the optimal point of $(\alpha, \sigma)=(-3/2, 1)$ (see FIG. 3A-C, 4$^{th}$ time point=12 hrs of wakefulness). This further strengthens the claim for a direct relationship between avalanche dynamics and behavioral performance that is beyond a simple monotonic correlation with wakefulness.

As noted above, the values of $\sigma$ and $\alpha$ depend on the analysis time scale, which in turn is linked to the use of an electrode array with a particular interelectrode distance, which is linked to the propagation velocity of neuronal activity. Thus, the changes observed in avalanche parameters with increase in wakefulness, could have resulted from changes in the effective time scale of activity propagation in the brain and not a change in the avalanche organization. As a control, the inverse of the propagation velocity, i.e. time between successive events on the array, was estimated using the mean time interval between consecutive events on the sensor array [11]. FIG. 3F depicts the mean IEI (inter-event-interval) as a function of time awake. It remains approximately constant around 5 ms, consistent with the estimate obtained from the plot of $\alpha$ vs. $\sigma$ (FIG. 2; 6 ms). Thus, the observed effects are indeed more likely to be directly related to deviations of the brain activity from neuronal avalanche dynamics, as can be induced by changes in the balance of excitation and inhibition.

The dependence of neuronal avalanche metrics on wake time was analyzed using EEG recordings of human subjects during an extended wake period of 36 hrs. The branching parameter and avalanche exponent increased with time awake, reflecting increased dominance of excitatory forces in the underlying network dynamics. This indication of excitation-inhibition imbalance is consistent with the prediction of the synaptic homeostasis hypothesis [7]. A strong correlation was also found between avalanche metrics and behavior as measured through reaction times, demonstrating that these metrics reflect meaningful features of brain dynamics and can be useful for predicting a subject's performance. Sleep deprivation has different effects on different subjects. Whereas some subjects show mild effects, others exhibit more dramatic effects. Continuous monitoring of the changes in avalanche metrics during wake time may be useful for identifying subjects that are more susceptible to the side-effects of sleep deprivation as well as for providing a warning message when a relevant threshold is crossed.

The findings of the present invention may be used to monitor the degree of potential dysfunction in subjects that experience prolonged periods of wakefulness on duty and in patients with sleep disorders. Traditional EEG technology relies on electrodes that are attached to the scalp using conducting gel, limiting its use in many practical applications. However, in recent years there were major advances in the new technology of dry EEG electrodes and there are by now FDA-approved commercially available headsets. These headsets can be directly used in many civil and military applications and they can also be easily integrated into helmets of soldiers and pilots. One limitation of these headsets is that they typically contain a small number of sensors. However, as demonstrated in FIG. 1, the power law behavior is evident even with smaller sets of sensors and does not require the full hd-EEG sensor set. The continuously recorded EEG can be evaluated online. If the deviation from expected avalanche dynamics reaches a critical threshold, an alert will be issued signaling that the subject is at risk of underperformance. Other applications include post-exercise analysis to identify individuals resilient to sleep deprivation or at risk.

Further, the avalanche metrics can be integrated with additional sources of information, such as the theta power or data from other physiological sensors, to make the decision even more accurate and less prone to artifacts.

Materials and Methods

The experiments described herein were carried out with, but are not limited to, the following materials and methods.

Experimental Design

The experimental design and data collection have been described in detail in [9] and are incorporated by reference herein. The experiment involved sixteen healthy participants (age=19-26) from the University of Wisconsin-Madison campus. All participants completed two experiments separated by at least 2 weeks, the order of which was randomly assigned and counter-balanced across subjects. In each experiment participants were asked to stay awake for at least 24 hrs and up to 36 hrs, during which they were engaged in a language task or a visuo-motor task (see [9] for more details). Here we focused on 5 datasets in which 3 subjects stayed awake for 36 hours.

The night before the experiment, participants were asked to go to bed at their usual bedtime, wake up at ~7:00, and arrive in the lab at 8:30 to prepare for hd-EEG recordings (256 electrodes, Electrical Geodesics Inc.). Participants completed a baseline EEG recording session at 10:00, followed by 11 EEG recording sessions in intervals of 3 hours. Between recording sessions, subjects completed 2-h periods of experimental tasks. After 36 hours they went to sleep and were woken up after 8 hrs. A final testing session was performed 30 min after they woke up (to reduce the influence of sleep inertia).

Each EEG session consisted of two 2-min eyes-open periods, interleaved by two 2-min eyes-closed periods (order counterbalanced across participants). At the beginning and at the end of each session, sleepiness was evaluated using self-rating questionnaires (Stanford Sleepiness Scale; [17]) and a 10-min psychomotor vigilance task (PVT; [18]). Participants performed the PVT (adapted version of [19]) for ~10 min while fixating a cross placed at the center of a computer screen. They were instructed to respond as quickly as possible to stop a millisecond counter that started to scroll at random intervals between 2 and 12 sec.

Measuring Neuronal Avalanches Using EEG

Neuronal avalanches can be identified in human subjects using the technologies of EEG and MEG [13, 20]. Here we follow the same steps as in [13]. The data were sampled at 500 Hz and bandpass filtered (1-150 Hz). Four channels that contained artifacts were removed. For each sensor, positive and negative excursions beyond a threshold of 3SD were identified. A single event was identified per excursion, at the most extreme value (maximum for positive excursions and minimum for negative excursions). The resulting time series of events was individually discretized with time bins of duration $\Delta t$. The timescale of the analysis, $\Delta t$, was explored systematically in multiples of $\Delta t_{min}=2$ ms, which was the inverse of the data acquisition sampling rate (500 Hz). A cascade was defined as a continuous sequence of time bins in which there was an event on any sensor, ending with a time bin with no events on any sensor. The number of events on all sensors in a cascade was defined as the cascade size. The avalanche size distribution's fit to a power law was obtained using the methods described in [21, 22].

The branching parameter, $\sigma$, was estimated by calculating the ratio of the number of events in the second time bin of a cascade to that in the first time bin. This ratio was averaged over all cascades for each subject with no exclusion criteria, $$\sigma = \frac{1}{N_{av}} \sum_{k=1}^{N_{av}} \frac{n_{events}(\text{2nd bin } k'\text{th avalanche})}{n_{events}(\text{1st bin } k'\text{th avalanche})} \quad (1)$$

where $N_{av}$ is the total number of avalanches in the dataset and $n_{events}$ represents the number of events in a particular bin. Note that for single bin cascades the second bin is an empty bin and therefore the corresponding ratio is 0.

Statistical Analysis

Correlations between avalanche metrics, time awake and reaction times were evaluated using linear regression and the corresponding p-values were calculated in each case.

Example 2: Changes in Neuronal Avalanches During Sustained Wakefulness in Humans and Rodents Described herein is a rat model of sleep deprivation. Using invasive recording technology and behavioral paradigms, it was demonstrated in the rat model that avalanche metrics change as a function of time awake as reported in humans.

The rat model was utilized to demonstrate that cortical dynamics in rats become supercritical, i.e., move away from avalanche dynamics, with prolonged sleep deprivation, which is congruent with the results presented for humans in FIG. 3A-FIG. 3F.

Sleep has been suggested as a homeostatic regulatory process that rebalances cortical excitability increased during wakefulness's (Huber, R. et al. 2013 Cereb Cortex, 23: 332-338; Tononi, G. & Cirelli, C. 2003 Brain research bulletin, 62: 143-150). The dependency of avalanche dynamics on the E-I balance (Shew et al., 2009 J. Neurosci., 29: 15595-15600; Shew et al., 2011 J. Neurosci.; 5: 55-63) predicts a progressive deviation towards a supercritical state as a function of time awake. Indeed, a recently observed alteration in critical brain dynamics during sustained wakefulness in humans suggests a pivotal role of sleep to maintain brain dynamics at a critical state (Meisel et al., 2013 J. Neurosci., 33: 17363-17372).

Described herein is a positive correlation between time awake, increase in branching parameter, and increase in reaction time in sleep deprived humans (see also, FIG. 3A-FIG. 3F). It was examined if similar to humans, rodents also undergo significant deviations from avalanche dynamics with sustained wakefulness, which are reset by sleep. This was examined by taking advantage of the insight into neuronal avalanches in the rodent brain using high-resolution LFP measured with MEAs.

Design and Data Analysis

4×8 MEAs (Neuronexus) were implanted into superficial layers of prefrontal cortex for chronic recordings in the awake, behaving rat. To monitor vigilance state, EEG and electromyogram (EMG) were simultaneously recorded. Rats were sleep deprived by the commonly used method of 'gentle handling' for up to 6 h (equivalent to up to 18 h time awake) during which MEA activity, EEG and EMG were recorded (Blackrock Systems) for off-line analysis. The LFP (1-100 Hz; sampling rate 500 Hz) was z-normalized, subjected to thresholding, and spatiotemporal clusters were identified for various temporal resolutions.

Results and Interpretation

Neuronal avalanche sizes exhibited a systematic shift towards larger avalanches leading to progressive distortion of the underlying power law in size distribution measured by kappa, κ, (Shew et al., 2009 J Neurosci, 29: 15595-15600) and increasing branching parameter σ as a function of time awake (FIG. 4A and FIG. 4B). The observed changes were reversed by consecutive sleep. These results suggest that sleep functions to tune cortical networks in the brain to a critical state where information processing is optimized.

Neuronal Avalanche Dynamics and Sleep

Figure 6:
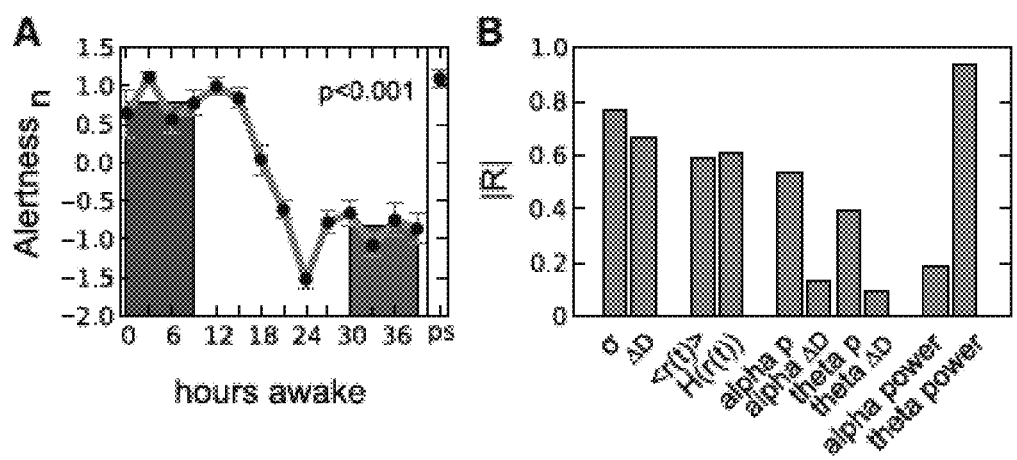
FIG. 6A is a bar chart. The colored bars correspond to averages of the four EEG recordings at 0-9 h (blue) and at 30-39 h (red) of wakefulness; p values indicate the difference between red and blue bars (two-tailed paired t test).
FIG. 6B is a bar chart. Of all metrics, theta spectral power and σ exhibit the highest correlation with alertness as quantified by the absolute correlation coefficient [R].

As demonstrated in Meisel (Meisel et al., 2013 The Journal of Neuroscience, 33(44):17363-17372, incorporated herein by reference), cortical dynamics progressively becomes supercritical with sleep deprivation. Specifically, Meisel demonstrated that the precise power-laws governing the cascading activity of neuronal avalanches and the distribution of phase-lock intervals in human electroencephalographic recordings are increasingly disarranged during sustained wakefulness. The results presented in FIG. 5A-FIG. 5D, which were obtained from humans, correlate with the results obtained from rats presented herein (FIG. 4A and FIG. 4B). Moreover, FIG. 6A-FIG. 6B demonstrate that the deviation from sigma (one of the critical avalanche measures) shows a high correlation with self-rated alertness in humans.

The results described herein in humans and rats demonstrate that a and size distributions change with sleep deprivation.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

REFERENCES

As should be understood, the citations above to one or more numbers within brackets (e.g., [1-3]) refers to the document(s) listed below first identified with a like number (thus, [1-3] above refers to the below listed Fenn et al.; Stickgold et al., and Walker et al.

DOCUMENTS

1. Fenn K M, Nusbaum H C, Margoliash D (2003) Consolidation during sleep of perceptual learning of spoken language. Nature 425: 614-616.
2. Stickgold R, James L, Hobson J A (2000) Visual discrimination learning requires sleep after training. Nature Neuroscience 3: 1237-1238.
3. Walker M P, Brakefield T, Morgan A, Hobson J A, Stickgold R (2002) Practice with sleep makes perfect: sleep-dependent motor skill learning. Neuron 35: 205-211.
4. Pilcher J J, Huffcutt A J (1996) Effects of sleep deprivation on performance: a meta-analysis. Sleep: Journal of Sleep Research & Sleep Medicine.
5. Harrison Y, Home J A (2000) The impact of sleep deprivation of decision making: A review. Journal of experimental psychology Applied 6: 236-249.
6. Drummond S P, Brown G G, Gillin J C, Stricker J L, Wong E C, et al. (2000) Altered brain response to verbal learning following sleep deprivation. Nature 403: 655-657.
7. Tononi G, Cirelli C (2006) Sleep function and synaptic homeostasis. Sleep medicine reviews 10: 49-62.
8. Cajochen C, Brunner D P, Krauchi K, Graw P, Wirz-Justice A (1995) Power density in theta/alpha frequencies of the waking EEG progressively increases during sustained wakefulness. Sleep 18: 890.
9. Hung C, Sarasso S, Ferrarelli F, Riedner B, Ghilardi M, et al. (2013) Local experience-dependent changes in the wake EEG after prolonged wakefulness. Sleep 36: 59-72.
10. Aeschbach D, Matthews J R, Postolache T T, Jackson M A, Giesen H A, et al. (1997) Dynamics of the human EEG during prolonged wakefulness: evidence for frequency-specific circadian and homeostatic influences. Neuroscience Letters 239: 121-124.
11. Beggs J M, Plenz D (2003) Neuronal avalanches in neocortical circuits. J Neurosci 23: 11167-11177.
12. Harris T E (1989) The theory of branching processes. New York: Dover Publications.
13. Shriki O, Alstott J, Carver F, Holroyd T, Henson R N, et al. (2013) Neuronal Avalanches in the Resting MEG of the Human Brain. J Neurosci 33: 7079-7090.
14. Plenz D (2012) Neuronal avalanches and coherence potentials. The European Physical Journal-Special Topics 205: 259-301.
15. Shew W L, Yang H, Petermann T, Roy R, Plenz D (2009) Neuronal avalanches imply maximum dynamic range in cortical networks at criticality. J Neurosci 29: 15595-15600.
16. Shew W L, Yang H, Yu S, Roy R, Plenz D (2011) Information capacity and transmission are maximized in balanced cortical networks with neuronal avalanches. J Neurosci 31: 55-63.
17. Herscovitch J, Broughton R (1981) Sensitivity of the stanford sleepiness scale to the effects of cumulative partial sleep deprivation and recovery oversleeping. Sleep 4: 83.
18. Basner M, Dinges D F (2011) Maximizing sensitivity of the psychomotor vigilance test (PVT) to sleep loss. Sleep 34: 581.
19. Dinges D F, Powell J W (1985) Microcomputer analyses of performance on a portable, simple visual RT task during sustained operations. Behavior Research Methods, Instruments, & Computers 17: 652-655.
20. Palva J M, Zhigalov A, Hirvonen J, Korhonen O, Linkenkaer-Hansen K, et al. (2013) Neuronal long-range temporal correlations and avalanche dynamics are correlated with behavioral scaling laws. Proceedings of the National Academy of Sciences 110: 3585-3590.

21. Klaus A, Yu S, Plenz D (2011) Statistical analyses support power law distributions found in neuronal avalanches. PLoS ONE 6: e19779.
22. Clauset A, Shalizi C R, Newman M E J (2007) Power-law distributions in empirical data. arXiv:07061062v2.

What is claimed is:

1. A method of determining the degree of sleep deprivation in a subject comprising:
   (a) performing an electrocephalogram (EEG) using sensors provided on the subject;
   (b) determining, by at least one processing device, an avalanche exponent α or a branching parameter σ from signals output by the sensors, wherein α is a slope of a size distribution of a synchronized neuronal activity and σ is a ratio of successively propagated synchronized neuronal activity;
   (c) determining, by the at least one processing device, a deviation in α or σ as determined from a pre-determined value of α or σ at rest, wherein:
      the pre-determined value of α is −3/2, and
      the pre-determined value of σ is 1;
   (d) repeating steps (a)-(c) one or more times;
   (e) determining, by the at least one processing devices, the degree of sleep deprivation in the subject, wherein a change in α or σ from the pre-determined value of alpha (α) or sigma (σ) indicates the degree of sleep deprivation in the subject;
   (f) providing, by the at least one processing devices, an alert when the degree of sleep deprivation determined the subject crosses a critical threshold that the subject is at risk of underperformance, and outputting a recommendation the subject undergo a period of recovery sleep; and
   (g) repeating steps (a) through (e) one or more times if the subject has undergone a period of recovery sleep to determine whether the period of recovery sleep has diminished the degree of sleep deprivation determined in the subject below the critical threshold.

2. The method of claim 1, wherein the subject with the deviation in α or σ as determined from the pre-determined value of α or σ performs a psychomotor vigilance task.

3. The method of claim 1, further comprising determining, by the at least one processing device, a magnitude and spatial distribution of theta power in the signals output by the sensors.

4. The method of claim 1, further comprising gathering data from other physiological sensors.

5. The method of claim 1, wherein the method is operational with hardware or software or a combination thereof.

6. The method of claim 1, wherein step (a) further comprises:
   (i) filtering the signals output from the sensors;
   (ii) the sensors include multiple EEG electrodes, and positive/negative threshold crossings at each EEG electrode are detected;
   (iii) clustering threshold crossings on the EEG electrodes on a pre-determined time scale; and
   (iv) calculating the cluster size distribution for determining α, or calculating a ratio of successive threshold crossings for determining σ.

7. The method of claim 6, wherein the EEG is continuously recorded at more than one site.

8. The method of claim 6, wherein the EEG is filtered between 1-100 Hz.

9. The method of claim 6, wherein the time scale is 1-50 ms.

10. The method of claim 1, wherein the deviation in α or σ as determined from the pre-determined value of α or σ indicates the presence of sleep deprivation in the subject when the change is outside of a tolerance range of 10% deviation from the pre-determined value of α or σ.

11. The method of claim 1, wherein the sensors include multiple dry electrodes of a headset, wherein the dry electrodes are individually isolated and amplified, wherein the headset is wearable in a non-laboratory setting.

12. The method of claim 1, further comprising:
   (h) identifying the time when α and σ are determined to deviate from their pre-determined values at rest.

* * * * *